(12) United States Patent
Vijaykalyan et al.

(10) Patent No.: US 8,526,693 B2
(45) Date of Patent: *Sep. 3, 2013

(54) SYSTEMS AND METHODS FOR MACHINE LEARNING BASED HANGING PROTOCOLS

(75) Inventors: Yeluri Vijaykalyan, Sunnyvale, CA (US); Denny Lau, Emeryville, CA (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,094

(22) Filed: Mar. 20, 2012

(65) Prior Publication Data

US 2012/0189180 A1    Jul. 26, 2012

Related U.S. Application Data

(63) Continuation of application No. 12/240,733, filed on Sep. 29, 2008, now Pat. No. 8,165,368.

(51) Int. Cl.
*G06K 9/00* (2006.01)

(52) U.S. Cl.
USPC ........................................................ 382/128

(58) Field of Classification Search
USPC ............ 382/128–132, 156; 705/2, 5; 706/15
See application file for complete search history.

(56) References Cited

U.S. PATENT DOCUMENTS

| | | | |
|---|---|---|---|
| 7,995,854 B2 * | 8/2011 | Friedhoff et al. | 382/260 |
| 2003/0187689 A1 | 10/2003 | Barnes et al. | |
| 2004/0202387 A1 | 10/2004 | Yngvesson | |
| 2006/0104495 A1 * | 5/2006 | Cathier et al. | 382/128 |
| 2006/0135865 A1 | 6/2006 | Bharara et al. | |
| 2006/0146071 A1 | 7/2006 | Morita et al. | |
| 2007/0063998 A1 | 3/2007 | Mahesh | |
| 2007/0064984 A1 | 3/2007 | Vassa et al. | |
| 2007/0127795 A1 | 6/2007 | Lau et al. | |
| 2007/0159962 A1 | 7/2007 | Mathavu et al. | |
| 2007/0197909 A1 | 8/2007 | Kariathungal et al. | |
| 2008/0025585 A1 | 1/2008 | Novatzky et al. | |
| 2008/0117230 A1 | 5/2008 | Wegenkittl et al. | |
| 2010/0080427 A1 | 4/2010 | Yeluri et al. | |

FOREIGN PATENT DOCUMENTS

WO    2006094862    9/2006

OTHER PUBLICATIONS

Luo et al., "Automatic Image Hanging Protocol for Chest Radiograph in PACS," IEEE Transactions on Information Technology in Biomedicine, vol. 10, No. 2, Apr. 2006. (10 pages).

(Continued)

*Primary Examiner* — Nathan Ha
(74) *Attorney, Agent, or Firm* — Hanley, Flight and Zimmerman, LLC.

(57) ABSTRACT

Certain embodiments of the present invention provide methods and systems for determining a hanging protocol for display of clinical images in a study. Certain embodiments provide a method for determining a hanging protocol for clinical image display. The method includes capturing one or more high level characteristics for an image study based on relationships between images in the study. The method also includes identifying one or more low level characteristics for individual images in the image study. The method further includes classifying the image study based on a combination of the high level characteristics and the low level characteristics. The method additionally includes determining a hanging protocol for the image study based on the classifying. The method includes providing the hanging protocol for display of images in the image study.

20 Claims, 5 Drawing Sheets

(56) References Cited

OTHER PUBLICATIONS

Krupinski et al., "Choosing a Radiology Workstation: Technical and Clinical Considerations," Radiology, vol. 242: No. 3, Mar. 2007. (12 pages).

Morioka et al., "Disease Specific Intelligent Pre-fetch and Hanging Protocol for Diagnostic Neuroradiology Workstations," Department of Radiological Sciences, University of California, Los Angeles. (6 pages), Jan. 1, 2001.

European Patent Office, European Search Report and Opinion, issued in connection with application No. 09169893.6-2201, dated Dec. 17, 2009. (14 pages).

United States Patent and Trademark Office, "Notice of Allowance," issued in connection with U.S. Appl. No. 12/240,733, mailed on Dec. 21, 2011, 8 pages.

United States Patent and Trademark Office, "Restriction Requirement," issued in connection with U.S. Appl. No. 12/240,733, mailed on Sep. 1, 2011, 6 pages.

\* cited by examiner

SYSTEMS AND METHODS FOR MACHINE LEARNING BASED HANGING PROTOCOLS

RELATED APPLICATIONS

The present application claims the benefit of priority to U.S. patent application Ser. No. 12/240,733, filed on Sep. 29, 2009, entitled "SYSTEMS AND METHODS FOR MACHINE LEARNING BASED HANGING PROTOCOLS", which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to hanging protocol configuration in a picture archiving and communication system. In particular, certain embodiments of the present invention relate to machine learning based hanging protocol configuration in a picture archiving and communication system.

Healthcare environments, such as hospitals or clinics, include clinical information systems, such as hospital information systems ("HIS") and radiology information systems ("RIS"), and storage systems, such as picture archiving and communication systems ("PACS"). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

Current PACS systems use general techniques known as "hanging protocols" to format display or layout of images. Hanging protocols allow a user to display images based on modality, anatomy, and procedure. Hanging protocols present a perspective or view to a user, such as a radiologist. Images may be grouped according to characteristics such as DICOM series or series number.

Additionally, PACS systems attempt to prepare images for viewing by users by applying a series of processing steps or functions included in a Default Display Protocol ("DDP"). A DDP is a default workflow that applies a series of image processing functions to image data to prepare the image data for presentation to a user on a particular monitor configuration. DDPs typically include processing steps or functions that are applied before any diagnostic examination of the images. A DDP may be based on a type of imaging modality used to obtain the image data, for example. In general, a DDP attempts to present image data in a manner most useful to many users.

Currently, a hanging protocol or DDP algorithm in PACS applications uses individual data elements of an image's DICOM header and HL-7 order information to classify a study type and determine how the study should be displayed.

BRIEF SUMMARY OF THE INVENTION

Certain embodiments of the present invention provide methods and systems for determining a hanging protocol for display of clinical images in a study.

Certain embodiments provide a method for determining a hanging protocol for clinical image display. The method includes capturing one or more high level characteristics for an image study based on relationships between images in the study. The method also includes identifying one or more low level characteristics for individual images in the image study. The method further includes classifying the image study based on a combination of the high level characteristics and the low level characteristics. The method additionally includes determining a hanging protocol for the image study based on the classifying. The method includes providing the hanging protocol for display of images in the image study.

Certain embodiments provide a system for displaying clinical images for review. The system includes an input receiving one or more images in an image study for display. The system also includes a machine learning engine selecting a hanging protocol for display of the one or more images. The machine learning engine captures one or more high level characteristics for the image study based on relationships between images in the study. The machine learning engine identifies one or more low level characteristics for individual images in the image study. The machine learning engine classifies the image study based on a combination of the high level characteristics and the low level characteristics. The machine learning engine determines a hanging protocol for the image study based on the classifying. The system further includes an output providing the hanging protocol for use in displaying the one or more images.

Certain embodiments provide a machine-readable storage medium including a set of instructions for execution on a processor. The set of instructions includes an input routine receiving one or more images in an image study for display. The set of instructions also includes a machine learning routine selecting a hanging protocol for display of the one or more images. The machine learning routine captures one or more high level characteristics for the image study based on relationships between images in the study. The machine learning routine identifies one or more low level characteristics for individual images in the image study. The machine learning routine classifies the image study based on a combination of the high level characteristics and the low level characteristics. The machine learning routine determines a hanging protocol for the image study based on the classifying. The set of instructions further includes an output routine providing the hanging protocol for use in displaying the one or more images.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide systems and methods for automatic creation of hanging protocols based on general, high-level characteristics rules. Certain embodiments provide hanging or display protocols that can continue to adapt to a user's needs as image acquisition changes.

Hanging/display protocol rules are configured for variable such as modality, body part(s), exam procedure(s), historical count, monitor count, and the like. Accounting for many variables involves many permutations for hanging protocols. Additionally, typical studies now include several series rather than individual images. Instead of examining DICOM header information for a particular image, at least some relationship information for an image series and/or study can be captured and used to determine an appropriate hanging protocol. Using high level characteristics as guidelines for hanging/display protocols can help eliminate explicit rules for all of the individual variables listed above.

High-level characteristics can also be used to model an imaging study. The high level characteristics are determined based on image series information and a relationship between the series of images, for example. Then, the high level conceptual model of the study is mapped to a display layout based on machine learning algorithm(s). Certain embodiments provide machine learning based algorithm relying on a probabilistic model that can accommodate inexact matches, for example.

Certain embodiments use high level characteristics that dictate rules for display rather than relying on individual Digital Imaging and Communications in Medicine ("DICOM") standard data elements so that the rules are robust to changes in image acquisition techniques. In certain embodiments, high level characteristics do not change much over time so high level characteristics are more robust to introduction of new acquisition techniques. In certain embodiments, high level characteristics about an imaging study are determined based on information from a series of imaging in the study and the relationships between series of images. In certain embodiments, high level concept models are more resilient to small deviations in image acquisition techniques and therefore can be more accurate in classifying the image study.

Certain embodiments use machine learning techniques to map a high level concept model to image display layout(s). Machine learning techniques allow for introduction of new high level models or layouts and can adaptively evolve based on changes without manual changing of the rules.

Figure 1:
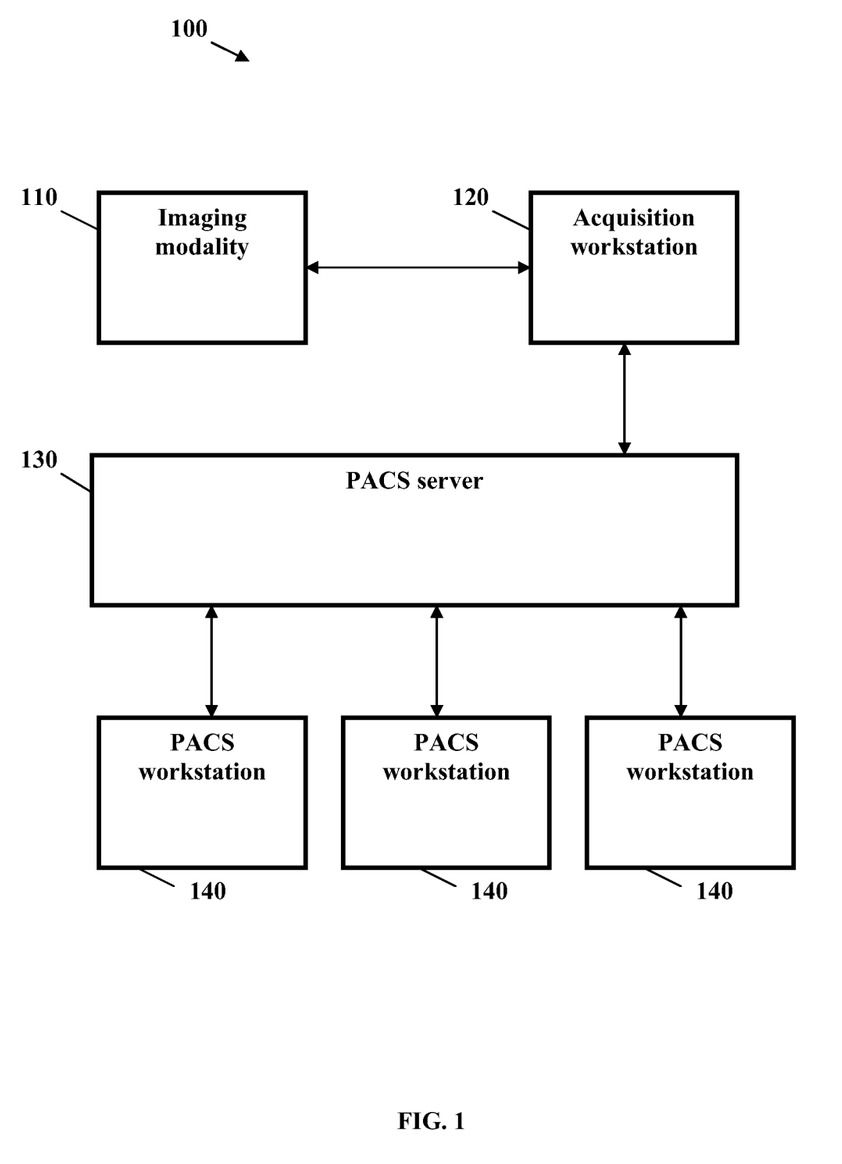
FIG. 1 illustrates an exemplary picture archiving and communication system used in accordance with an embodiment of the present invention.

FIG. 1 illustrates an exemplary Picture Archiving and Communication System (PACS) 100 used in accordance with an embodiment of the present invention. The PACS system 100 includes an imaging modality 110, an acquisition workstation 120, a PACS server 130, and one or more PACS workstations 140. The system 100 may include any number of imaging modalities 110, acquisition workstations 120, PACS server 130 and PACS workstations 140 and is not in any way limited to the embodiment of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography ("CR") image of a patient's chest. A radiologist or user may then examine the image for any objects of interest, such as tumors, lesions, etc., for example.

The PACS workstations 140 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In an embodiment, the PACS system 100 includes a perspectives manager capable of being used for reviewing images via a plurality of perspectives. The PACS server 130 and/or a PACS workstation 140 may include the perspectives manager, or the perspectives manager may be implemented in a separate system. In an embodiment, each PACS workstation 140 may include a perspectives manager.

In operation, for example, a user, such as a radiologist, selects a set of images, such as screening mammogram images, chest screening images and/or other computed radiography ("CR"), digital radiography ("DR"), and/or digital x-ray ("DX") screening images, to review at a PACS workstation 140. The images may be displayed in a default perspective and/or a customized perspective, for example.

As described above, a user may wish to apply additional processing steps to one or more images to further enhance features in the image. For example, a user may desire to apply additional processing functions or steps to an image in order to alter the presentation of an image in conformance with the user's confidence level for making an accurate diagnosis. In other words, different users may desire to apply different or additional processing steps than are included in a default image processing workflow.

The additional image processing step(s) may include any image processing step useful to prepare an image for a diagnostic examination. For example, as described above, an image processing step (as a default image processing step or an additional image processing step) can include flipping an image, zooming in an image, panning across an image, and altering one or more of a window, a level, a brightness and a contrast setting of an image. Image data may be displayed on a PACS workstation 140 using the same and/or different processing, display protocol, and/or perspective as other image(s), for example.

PACS workstations 140 may retrieve or receive image data from server 130 for display to one or more users. For example, a PACS workstation 140 may retrieve or receive image data representative of a computed radiography image of a patient's chest. A radiologist may then examine the image as displayed on a display device for any objects of interest such as, for example, tumors, lesions, etc.

PACS workstations 140 are also capable of or configured to retrieve and/or receive one or more hanging protocols from server 130. For example, a default hanging protocol may be communicated to PACS workstation 140 from server 130. A hanging protocol may be communicated between server 130 and a PACS workstation 140 over a wired or wireless connection, for example.

In general, PACS workstations 140 may present images representative of image data retrieved and/or received from server 130. PACS workstations 140 may present the images according to a hanging protocol. As described above, a hanging protocol is a set of display rules for presenting, formatting and otherwise organizing images on a display device of a PACS workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a PACS workstation 140 to display an anterior-posterior ("AP") image adjacent to a lateral image of the same anatomy. In another example, a hanging protocol may direct PACS workstation 140 to display the AP image before displaying the lateral image. In general, a hanging protocol dictates the spatial and/or temporal presentation of a plurality of images at PACS workstation 140.

A hanging protocol may differ from a default display protocol ("DDP"). However, the terms may also be used interchangeably and/or in overlapping circumstances. In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or functions that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users.

Conversely, applying a hanging protocol to image data may or may not alter the appearance of an image (based on the image data), but may instead dictate how the image(s) is (are) presented, as described above.

Server 130 may store a plurality of hanging protocols and/or DDPs. The hanging protocols and/or DDPs that are stored at server 130 and have not yet been modified or customized are default hanging protocols/DDPs. A default hanging protocol and/or DDP may be selected from a plurality of default hanging protocols and/or DDPs based on any number of relevant factors such as, for example, a manual selection, a user identity, and/or pre-processing of the image data.

Specifically, a default hanging protocol and/or DDP may be selected based on a manual selection simply by communicating the default protocol once a user has selected that particular protocol. The user may make the selection, for example, at a PACS workstation 140.

In another example, a default protocol may be selected based on a user identity. For example, a user may have a preferred DDP. The DDP may have been customized to meet the user's preferences for a particular temporal and/or spatial layout of images. Once a user gains access to a PACS workstation 140 (for example, by entering a correct login and password combination or some other type of user identification procedure), the preferred DDP may be communicated to the PACS workstation 140, for example.

In another example, a default protocol may be selected based on pre-processing of image data. Pre-processing of image data may include any image processing known to those of ordinary skill in the art that prepares an image for review by a user. Pre-processing may also include, for example, a computer-aided diagnosis ("CAD") of image data. CAD of image data may include a computer (or similar operating unit) automatically analyzing image data for objects of interest. For example, a CAD may include a software application that analyzes image data for nodules in images of lungs, lesions, tumors, etc. However, a CAD application can include any automatic analysis of image data known to those of ordinary skill in the art.

For example, a default hanging protocol that corresponds to CAD findings of lung tumors may provide for the presentation of the posterior-anterior ("PA") and lateral lung images adjacent to each other followed by the presentation of the computed tomography ("CT") lung images, followed by the magnetic resonance ("MR") lung images, for example. In general, a default hanging protocol that corresponds to CAD findings is designed to present images in a spatial and/or temporal layout that is useful to a radiologist. For example, a radiologist may be greatly assisted in his or her review of the CAD findings by viewing the PA and lateral lung images adjacent to each other, followed by previously acquired multi-slice CT and MR images of the lungs.

Therefore, based on CAD findings, a default protocol may be selected from a plurality of default protocols and applied at a workstation 140 in order to present images to a user.

PACS users often wish to run multiple applications on a PACS workstation 140. In addition to a primary PACS workflow or interface application, a user may wish to access other applications such as surgical planning tools, scheduling tools, electronic mail viewers, image processing tools, and/or other tools. For example, PACS users often like to use a PACS workflow engine while viewing electronic mail and accessing information on the Internet. Users of an integrated RIS/PACS system may wish to access both RIS and PACS applications simultaneously. Typically, however, the PACS application occupies all active display area and hides other applications running on the workstation 140. For example, in a PACS workstation 140 having three monitors, the PACS workflow application occupies all three monitors. When an application is initiated, another application may be displaced, or the application may be launched in a sub-optimal display area. For example, a user may launch a data management or diagnostic processing software at a three-monitor PACS workstation 140, and the application may launch on a color monitor, displacing images displayed on the color monitor. Typically, a user would have to manually reorganize applications to display the management application on a grayscale monitor and the images on the higher resolution color monitor.

Certain embodiments provide an adaptable PACS system 100 accommodating a plurality of displays such that each display operates with a separate display window. All display windows are controlled internally by a primary window that is transparent to users. The primary, transparent window tracks which window or windows have the PACS application and which window(s) have other applications and/or data. Thus, the PACS application and other applications may be simultaneously displayed on a plurality of displays.

Certain embodiments provide dynamic configuration of displays associated with PACS workstation 140. The primary window allows interaction or application(s) and data across multiple windows. The PACS workstation 140 operates a transparent, primary window including a plurality of windows across a plurality of displays.

Selection of a hanging/display protocol on a PACS workstation may be based on a plurality of criteria, such as a number of connected displays, a modality, an anatomy, and a procedure, for example. Based on these criteria, a user may create multiple protocols with one default protocol used to display an image study. For example, a hanging protocol may be created for a particular display configuration. A user creates different hanging protocols to properly display a study on different display configurations.

However, certain embodiments allow creation of a protocol including a plurality of perspectives or views, for example. Using one protocol with multiple perspectives/views, a user may associate different perspectives/views for different display configurations with the protocol. For example, a hanging protocol may include multiple perspectives with one default perspective. The default perspective may be used to display a study unless otherwise specified and/or determined manually or automatically, for example.

In certain embodiments, hanging protocols with perspectives/views may use one or more criteria to select a protocol for display. For example, a modality, an anatomy or body part, a procedure, and/or a default view for a display configuration, may be used to select an appropriate display protocol. For example, a display protocol includes a perspective/view with multiple options depending upon monitor configuration. A user may create a hanging protocol with different view for different display configurations, for example. A user does not have to create different hanging protocols for different monitor configurations but may instead create additional views with the existing hanging protocol. In certain embodiments, a user may switch between different perspectives/views after opening a study.

In certain embodiments, perspectives are views or layouts indicating visual component positioning and interactions between images and/or applications based on workflow, for example. Medical perspectives may be used to create a plurality of benefits for. For example, perspectives may provide patient context sharing between different image(s) and/or application(s) that a user views. Additionally, for example, perspectives provide an ability to easily switch between different configurations or perspectives based on which images and/or applications a user wishes to view at any given point. Furthermore, for example, perspectives provide an ability to store or "remember" specific workflow steps. Perspectives provide a mechanism to save and display information relevant to a particular user, group, and/or function, for example. Perspectives may be used to display images and other data for a particular resolution, display type, and/or other configuration, for example.

Perspectives may be used to logically group different images and/or other data or applications. For example, perspectives may be defined for images, examination results, laboratory data, patient history data, structured report data, DICOM data, and/or other data or applications, for example. Rules, configuration options, and/or other criteria may be defined in order to define perspectives. In certain embodiments, perspectives do not eliminate or change information but rather order information in a certain way. For example, information important to a user may be displayed first, with additional information available via different perspectives. In certain embodiments, perspectives may be created automatically based on user selection or other configuration information, for example. In certain embodiments, a perspective may work together with a rules-based context manager to filter and display information.

In certain embodiments, medical are software components that save visual component positioning and interactions between medical applications and data based on workflow. Medical application perspectives are a mechanism used to create a plurality of benefits for users. For example, perspectives may provide patient context sharing between different applications, data and/or other components that a user views. Additionally, for example, perspectives provide an ability to switch between different configurations or perspectives based on which applications, data and/or other components a user wishes to view at any given point. Furthermore, for example, perspectives provide an ability to store or "remember" specific workflow steps. Perspectives provide a mechanism to save and display information relevant to a particular user, group, and/or function, for example.

Perspectives that may be saved by and/or for one or more users. For example, a perspective may include viewing an exam worklist on a color monitor, one or more images displayed on one or more diagnostic monitors, and a report editor on the bottom of the color monitor. For example, another perspective may include viewing related prior report(s) on the color monitor, related prior image(s) on one diagnostic monitor, and current image(s) on another diagnostic monitor. For example, a perspective may show viewing all labs and allergies for a period of time (e.g., two months) for a patient on the color monitor and viewing current image(s) on the diagnostic monitor(s). As another example, a perspective may include viewing any maximum intensity projection/multiplanar reconstruction ("MIP/MPR") image set for a current exam on a diagnostic monitor.

In certain embodiments, users may "switch to" or "be assigned" a medical perspective on the fly. Based on available perspectives, a user may toggle between perspectives to read an exam or other data. A user may toggle between available perspectives using a mousing device, keyboard shortcuts, gaze tracking, and/or voice command, for example. In certain embodiments, specific workflows of individual radiologists and/or cardiologists may be stored so that each radiologists/cardiologists uses the same workflow through the same sequence of perspectives wherever the user logs in. Thus, a user has the advantage of reading exams and other data quickly and efficiently on any diagnostic workstation, for example.

In certain embodiments, software, firmware and/or hardware may verify a user's right to access one or more of the applications and/or perspectives. For example, if a user logs on to a system with perspectives, based on previous saving of a default perspective, the user is logged on automatically into RIS, PACS, and EMR systems.

Thus, a user may access relevant prior history for a patient (e.g., images and reports). Using different perspectives the user has already created, the user may switch between perspectives to view desired information. The medical application perspectives may be delivered to the user in a variety of ways. For example, perspectives may be delivered via a preselected set of components and/or workflows from a medical software and/or hardware provider. Perspectives may also be delivered via perspectives created by a system administrator. Additionally, a user may dynamically create perspectives during operation of the system 100 (i.e., "on the fly"). Thus, the user may select components and/or applications for display in viewable areas of one or more monitors based on workflow. The information/configuration may then be saved in one or more perspectives. The user may toggle between perspectives to read an exam or other data on a variety of devices such as displays and/or printers. The user may save perspectives, exams, reports, and/or other data, for example.

In an embodiment, a plurality of applications may be providing information to a radiologist, cardiologist and/or other user for diagnosis of a patient. One or more displays available to the user may not have enough screen space to display all of the information. Additionally, displaying all of the available information would be too crowded to be useful. Even if information is filtered with rules, too much information may still remain. Thus, a user may apply medical perspectives on a workstation to view information from a plurality of applications and systems. One perspective may be set up to show images and/or examination results from radiology, for example. Another perspective may be set up to show images and/or examination results from cardiology, for example. Another perspective may be set up to show images and/or examination results from imaging, for example.

Perspectives may be used to logically group different applications, for example. Rules, configuration options, and/or other criteria may be defined in order to define perspectives. Perspectives may be defined for images, examination results, laboratory data, patient history data, structured report data, DICOM data, and/or other data, for example. In certain embodiments, perspectives do not eliminate or change information but rather order information in a certain way. For example, information important to a user may be displayed first, with additional information available via different perspectives. In certain embodiments, a system may "learn" through user selection or other configuration information, for example, to create perspectives automatically without manual intervention by the user.

In certain embodiments, images in perspectives may be organized according to one or more criterion. For example, the default perspective includes a first set of images organized according to a default criterion, while the second perspective includes a second set of images organized according to a second criterion. The second criterion may be different from the default criterion, for example. Additionally, the second set of images may be a subset of the first or default set of images, which may include all available images for a subject, procedure, modality, and/or user, for example.

In certain embodiments, the criterion includes image attributes, such as procedure-specific image attributes. For example, the second perspective may be organized or laid out based on mammogram-specific image attributes found in image DICOM headers. Use of image attributes in determining a perspective layout allows precision in reproducing a perspective for each instance of a procedure, for example.

Additionally, a display protocol, such as a Default Display Protocol ("DDP"), may be adjusted for one or more displays based on content and/or a number of connected display(s). For example, if the PACS workstation 140 is reconfigured from a three monitor configuration to a one monitor configuration, the DDP may be modified accordingly. Certain embodiments adapt a DDP based on application(s) closed and/or opened as well as window(s) activated and/or deactivated. For example, a DDP may determine what information is displayed to a user. A DDP may adapt based on a number of available monitors and a number of images to be displayed, for example (e.g., four images are shown on one available display; eight images are shown on two available displays, etc). PACS workstation 140 may configure a DDP for any multi-monitor full screen and/or partial screen applications. Additionally, one or more applications may be resized on a single screen (e.g., minimize, maximize, and/or resize).

A hanging protocol or DDP algorithm for PACS application may use individual data elements of the DICOM header and HL-7 order information to classify an image study type and determine how the study should be displayed one or more screens. Such a hanging protocol algorithm, however, includes many shortcomings. One of its shortcomings is that the current protocol algorithm cannot adapt to new study types or changes in image acquisition methodology. It would be difficult to capture all the rules and exceptions for current and future study types and translate them into a hanging protocol algorithm. The current algorithm only uses information from the image to model the study. This information is often insufficient to classify the study accurately to find an improved or more optimal layout.

Instead, it is better if there is additional information used to model the study. The additional information can be derived from relationships between the different images and different series in the study. Then, instead of using strict rules to map from a model of the study to the display layout, machine learning algorithms can be used that can continue to learn and evolve based on new acquisitions and be more robust to exceptions that could cause ambiguity. It is more useful to capture the high level characteristics of the study and classify them based on the high level characteristics in addition to the low level DICOM data elements that are currently used. These high level characteristics along with the data elements used currently can more fully describe the image study and model the study more accurately.

High level characteristics of an image study include, for example, detection method, number of relevant images based on the detection method, and image resolution versus monitor resolution.

When radiologists view images on their image review workstations, the images are displayed in a layout to facilitate efficient detection of abnormal anatomical or physiological features. Detection methods include a comparison of a current image study with one or more historical studies. Other detection methods include an ease to view a three-dimensional ("3D") dataset from different perspectives (e.g., axial, coronal, sagittal, oblique, etc). Another example of a detection method is an ease to extrapolate 3D information based on a two-dimensional ("2D") image of a 3D model (e.g., a volume rendering). Other detection methods include pre- and post-contrast injection detection, pre- and post-exercise detection, and temporal based navigation to illustrate physiological functions.

With temporal-based navigation, based on the imaging modality and acquisition techniques, different criteria are used to detect abnormalities. Different methods for detecting abnormalities involve different image layouts. For example, if a patient has current and three historical 2D chest radiographs acquired within the last seventy-two hours and one historical chest radiograph acquired from two months ago, then it would be best to display the current and the three recent images adjacent to each other to better visualize disease progression by detecting the differences between the images. If there is enough display area left, then the less relevant image from two months ago can be displayed. For a different patient with a different type of study, an image layout to better facilitate abnormality detection can be different from that of a patient with chest radiographs.

For a different method of detecting abnormalities, a different layout may be involved. For example, if a patient has current and historical computed tomography ("CT") contrast studies, then the current study's pre and post series can be displayed next to each other, and the previous study's pre and post contrast series can be displayed next to each other. Such a layout allows a radiologist to first compare the current pre and post contrast series to detect for abnormalities; then the radiologist can view a change compared to the previous study. Thus, for example, the pre and post contrast relationship between the two series is used to classify a type of layout used.

In certain embodiments, a rule is implemented such that, based on a detection method, a first image series that has a certain characteristic should be displayed in a location, and, given a detection method for the study, a series that is used for comparison should be displayed next to the first series and the like. In certain embodiments, relationship(s) between image series are used to determine display locations for the image series. The extra contextual information gathered from the relationships between different series of images improves accuracy of study modeling.

Certain embodiments provide a display rule based on a comparison of image resolution versus monitor resolution. In certain embodiments, the rule specifies that every pixel of an image should be displayed on a display. A calculation is done to determine how many images could fit on the display based on a number of pixels in the images and a number of pixels on the display(s). If the display monitor is 1200×1600 and the images are 512×512, then the monitor could at most fit six of these images on the display (assuming no other graphical user interface elements are displayed on the monitor). The rule is to fit as many relevant images as the detection method determines until there are not enough monitor pixels to display another image at full resolution. In the previous example, if there is a seventh image, then the seventh image would not be displayed. However, if there is a user setting that allows the smallest displayed image size to be one-quarter of the display area of monitor, then only four images would be displayed because this setting overrides the previous "fit as many images as the pixels will display" rule. If there are only three images, then only three images would be displayed, and the image display area for each image would be larger than if six images were displayed.

In certain embodiments, these high level characteristics can be determined based on relationships between DICOM header elements. Therefore, instead of only using the DICOM header elements, relationships between different series and different DICOM header elements are used to determine the high level characteristics for the study and then to classify the layout to be used for the study based on the high level characteristics. In certain embodiments, information from an image series and relationship information between image series are used at least in gathering high level information about an imaging study.

Based on a patient's different image series in current and previous studies, a hanging protocol algorithm can determine a methodology used to detect abnormalities. Rather than examining DICOM header information for a particular image, at least some relationship information for an image series and/or study is captured and used to determine an appropriate hanging protocol.

For example, a CT image series may include axial, coronal, saggital, and oblique images. A radiologist may want to see these differing image views at the same time to provide an approximation of a three-dimensional perspective. Exam information can enable identification of these images so that they can be displayed together.

As another example, a radiologist may be interested in images before and after contrast injection into a patient. Hanging or displaying the pre and post contrast injection images together helps allow the radiologist to identify abnormalities. Similarly, a radiologist may be interested in comparing displayed images obtained before and after a patient has exercised.

In certain embodiments, an exam image series may capture time (temporal) data to illustrate physiological function (e.g., a beating heart). A hanging protocol can recognize that the series is capturing time-based data and display or hang other time-based data as well.

In certain embodiments, high level characteristic information can be used to review a patient's exams to determine whether similar historical studies exist to be matched and displayed with newly obtained images.

In certain embodiments, DICOM header and image series description information can provide information as to what type of study has been obtained (e.g., temporal, etc.). An initial layout can be used to capture/learn how a particular user likes to display images. The information can be obtained/ stored so that it can be reproduced later as a hanging protocol. A user, such as a radiologist, can review, approve, and/or make changes to saved hanging protocol information, for example.

For example, if a user displays an exam, the hanging protocol also shows related prior exams. If a user is viewing an arterial exam, for example, certain embodiments can determine that the exam is an arterial exam based on DICOM header information and can then automatically display prior arterial exams.

Figure 2:
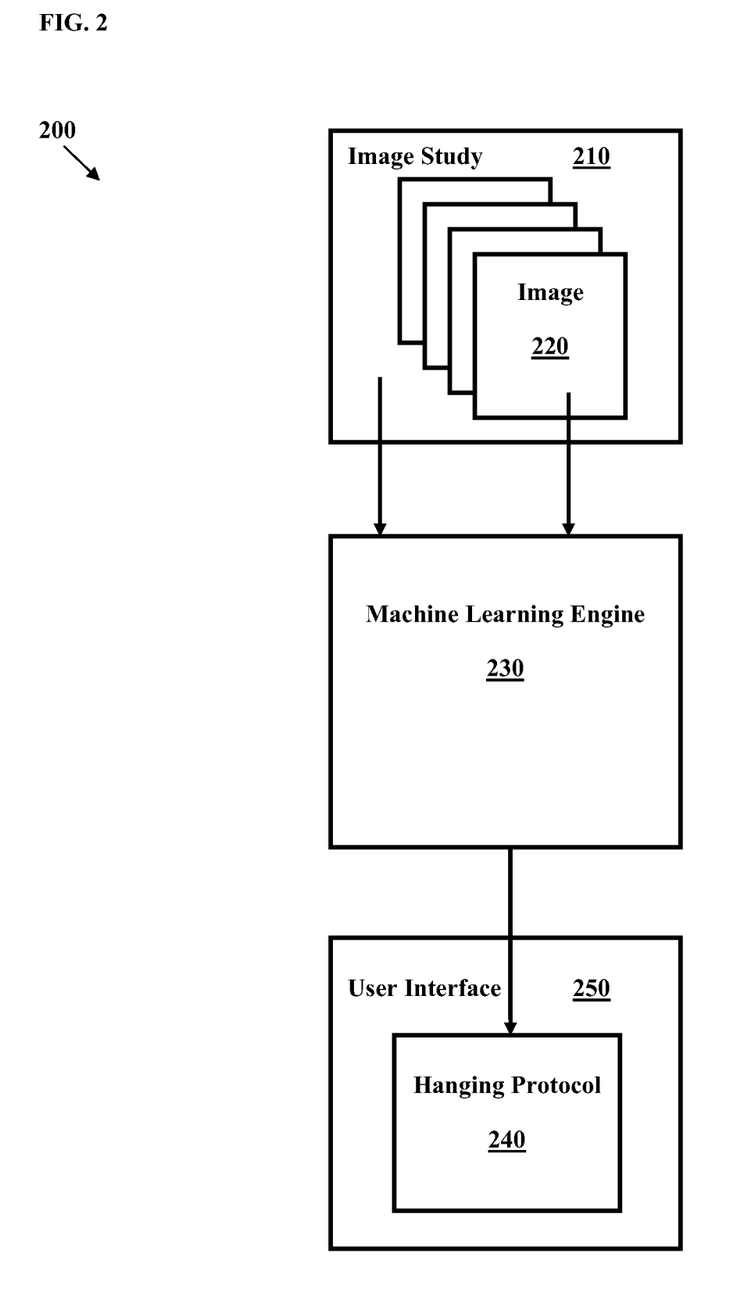
FIG. 2 depicts an example of a system for determination of an appropriate hanging or display protocol in accordance with an embodiment of the present invention.

FIG. 2 depicts an example of a system 200 for determination of an appropriate hanging or display protocol in accordance with an embodiment of the present invention. The example system 200 includes an image study 210 including study information, one or more individual images 220 including image DICOM header information, a machine learning engine 230, a hanging or display protocol 240, and a user interface 250. The components of the system 200 can be implemented in software, hardware, and/or firmware, for example.

In operation, the study 210 information and individual image 220 information are extracted from an image study and provided or otherwise made accessible to the machine learning engine 230. Based on initial user input and stored information gathered from past layouts, the engine 230 generates/ selects a hanging/display protocol 240 for displaying images and/or other data via the user interface 250. For example, an artificial neural network and/or other adaptive processing model can be used by the machine learning engine 230 to select an appropriate hanging protocol 240 based on available image header information, inter-image study information, and saved prior information.

In certain embodiments, a type of machine learning technique used is an artificial neural network. Hanging/display protocol algorithms can use DICOM header elements to determine high level characteristics for a study. Then, initially, a user lays out one or more image/series. Correlations between the high level characteristics and the user layout are stored in nodes of the artificial neural network. As the user makes changes to the layout over time, the artificial neural network nodes are updated, and the nodes continue to evolve. When the user displays a new study, the algorithms determine the high level characteristics of the study and classify them according to different layouts. In certain embodiments, artificial neural networks are used in systems wherein an algorithmic solution cannot be formulated; many examples of desired behavior can be obtained; and/or structure is selected from existing data, for example. Although artificial neural networks are discussed above, other forms of artificial intelligence, such as fuzzy logic, Boltzmann machine, Bayesian network, etc., can be used as machine learning techniques to determine an applicable hanging or display protocol.

For example, the engine 230 can account for one or more high level study characteristics including detection method used, number of relevant images for the detection method, and image resolution compared to monitor resolution based on relationships between image DICOM header elements. Based on a patient's different series in current and previous studies, for example, a hanging protocol algorithm used by the engine 230 can determine a methodology used to detect abnormalities. That methodology can help rank or select a hanging protocol for use in display of image(s) and/or other information on a user display. Different methodologies may involve different image layouts and thus different hanging protocols or DDPs, for example.

For example, if a patient has current and prior CT images, display priority and position may be given to the current and most recent prior image(s) as space and display quality allow. As another example, if images for a patient were obtained with and without contrast injection, a current study's pre and post contrast images may be displayed next to each other while previously study's pre and post contrast image series are displayed next to each other. Extra contextual information gathered from examining relationships between different series of images provides improved accuracy in modeling and display of a study.

Figure 3:
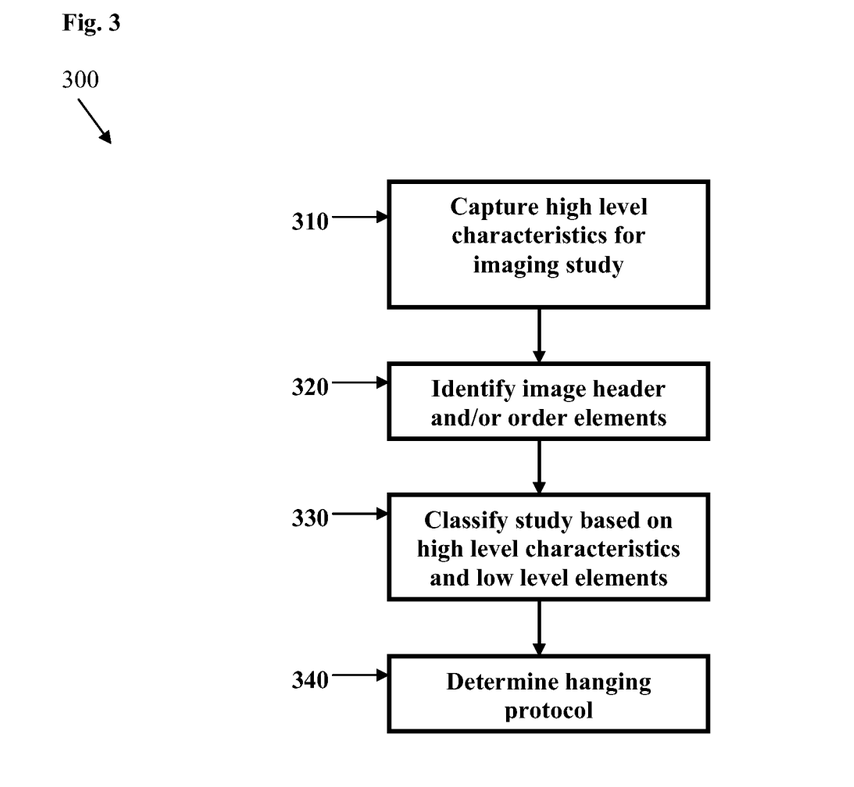
FIG. 3 illustrates a flow diagram for a method for determining a hanging protocol for display in accordance with an embodiment of the present invention.

FIG. 3 illustrates a flow diagram for a method 300 for determining a hanging/display protocol for display in accordance with an embodiment of the present invention.

At 310, high level characteristics for an imaging study are captured. For example, high level characteristic information can be derived from relationship(s) between different images and/or different series in the study. High level characteristic information may include detection method, number of relevant images based on the detection method, and/or image resolution as compared to monitor resolution, for example. For example, a detection method to identify abnormalities may include a current versus historical image study comparison, a display of multiple perspectives for a three-dimensional dataset, volume rendering of two-dimensional image slices into a three-dimensional model, comparison of images before and after contrast insertion, comparison of images before and after patient exercise, and temporal navigation of images to illustrate physiological function.

At 320, DICOM header elements and/or HL-7 order information for one or more individual images in the study are identified. For example, information such as modality, body part(s), exam procedure(s), historical count, monitor count, etc. can be obtained from image header and order information.

At 330, a study is classified based on the high level characteristics in addition to the low level DICOM and/or HL-7 data elements. Using high level characteristics in conjunction with individual image data elements can help to more fully describe the study and model the study more accurately while providing flexibility to accommodate inexact matches between studies and available hanging protocols.

At 340, a relevant hanging protocol/DDP is determined Different methods for detecting abnormalities may involve different image layouts, for example. Based on the detection method, a first image series that has a certain characteristic should be displayed in a first location, and, given the detection method for the study, a second image series that is used for comparison should be displayed next to the first series, etc. Extra contextual information gathered from relationships between different series of images improves accuracy in modeling the study.

An adaptive framework using both high level and low level information allows the framework to capture rules and exceptions for current and future study types and translate them into a hanging protocol algorithm. Instead of using strict rules to map from a model of a study to an image layout, machine learning algorithms are used that can continue to learn and evolve based on new acquisitions and be more robust to exceptions that could cause ambiguity in existing, fixed hanging protocol determinations, for example.

One or more of the steps of the method 300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 4:
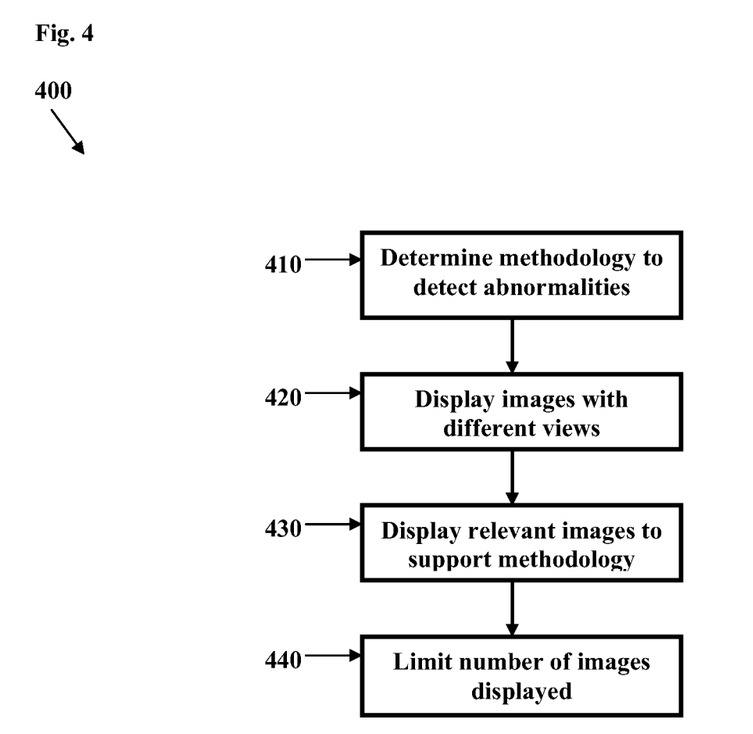
FIG. 4 illustrates a flow diagram for a method for applying a hanging protocol to a workstation display in accordance with an embodiment of the present invention.

FIG. 4 illustrates a flow diagram for a method 400 for applying a hanging/display protocol to a workstation display in accordance with an embodiment of the present invention.

At 410, a type of methodology to detect abnormalities is determined. For example, a methodology to detect abnormalities based on a comparison between cardiac images taken before a patient has exercised and after a patient has exercised is determined. A hanging protocol/DDP is selected based on the methodology and other available information regarding the study and its individual images.

At 420, images are displayed with different views of the patient. For example, cardiac images showing different views of the patient's heart are displayed. At 430, relevant images to support the methodology are displayed. For example, cardiac images taken before the patient exercised and after the patient exercised are displayed adjacent to each other based on view to allow better comparison by a reviewer.

At 440, a number of images displayed is limited by determining a minimum display size occupied by each image. For example, a minimum display size can be determined based on image resolution and monitor resolution to help ensure that pixels in the images are displayed on the monitor as well as the minimum displayed image size set by the radiologist. For example, if an image series includes data that is volumetric, then display the images in the series in stack mode. Volumetric data can be determined, for example, by checking that the DICOM header's image position data element difference from image to image is at a regular interval.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 5:
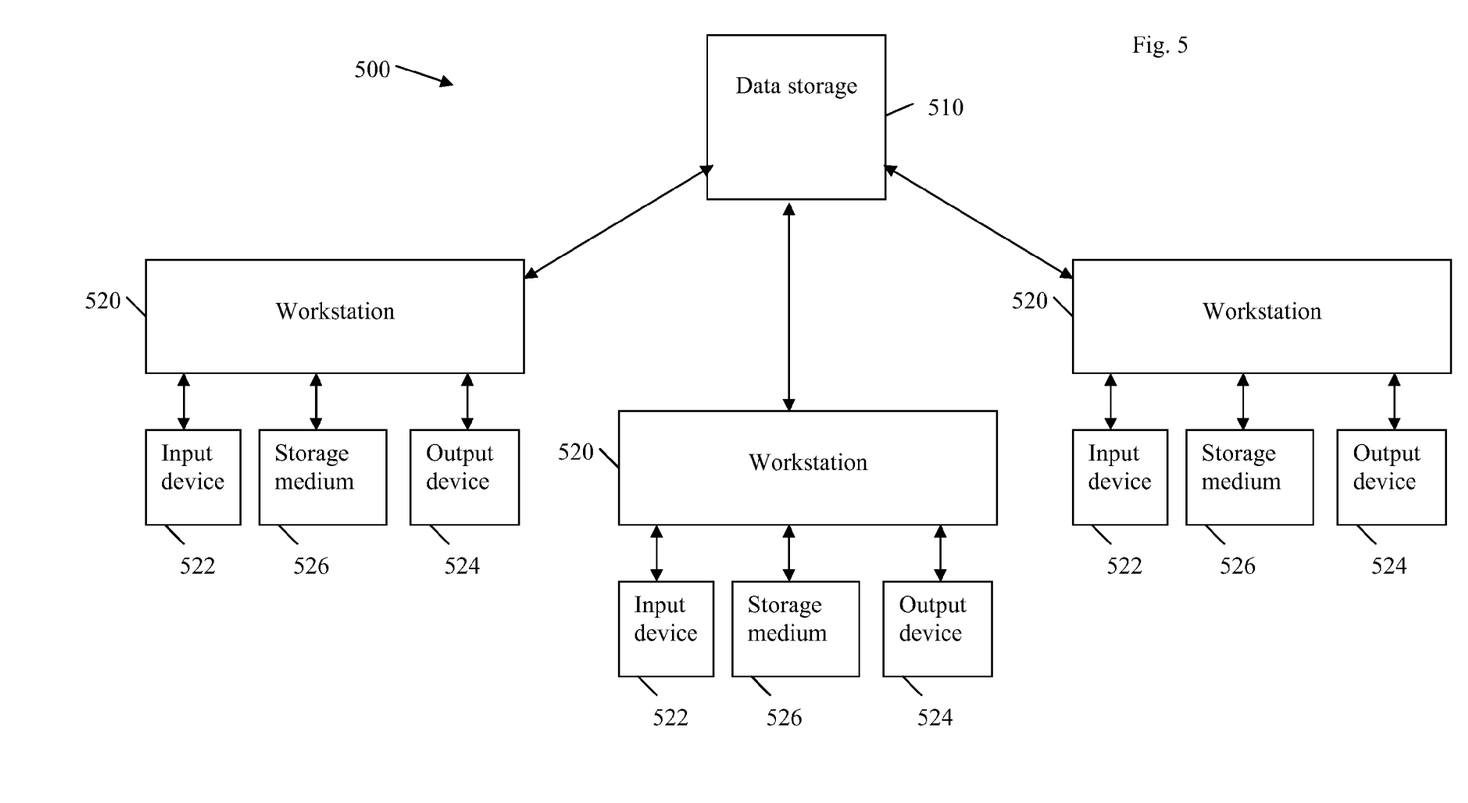
FIG. 5 illustrates an exemplary clinical information system that can be used in accordance with certain embodiments of the present invention.

Certain embodiments described above may be implemented on a clinical information system, such as the system 500 of FIG. 5. In certain embodiments, an interface including patient information and images may be viewed and/or constructed using a system such as system 500 including at least one data storage 510 and at least one workstation 520. While three workstations 520 are illustrated in system 500, a larger or smaller number of workstations 520 can be used in accordance with embodiments of the presently described technology. In addition, while one data storage 510 is illustrated in system 500, system 500 can include more than one data storage 510. For example, each of a plurality of entities (such as remote data storage facilities, hospitals or clinics) can each include one or more data stores 510 in communication with one or more workstations 520.

As illustrated in system 500, one or more workstations 520 can be in communication with at least one other workstation 520 and/or at least one data storage 510. Workstations 520 can be located in a single physical location or in a plurality of locations. Workstations 520 can be connected to and communicate via one or more networks.

Workstations 520 can be directly attached to one or more data stores 510 and/or communicate with data storage 510 via one or more networks. Each workstation 520 can be implemented using a specialized or general-purpose computer executing a computer program for carrying out the processes described herein. Workstations 520 can be personal computers or host attached terminals, for example. If workstations 520 are personal computers, the processing described herein can be shared by one or more data stores 510 and a workstation 520 by providing an applet to workstation 520, for example.

Workstations 520 include an input device 522, an output device 524 and a storage medium 526. For example, workstations 520 can include a mouse, stylus, microphone and/or keyboard as an input device. Workstations 520 can include a computer monitor, liquid crystal display ("LCD") screen, printer and/or speaker as an output device.

Storage medium 526 of workstations 520 is a computer-readable memory. For example, storage medium 526 can include a computer hard drive, a compact disc ("CD") drive, a USB thumb drive, or any other type of memory capable of storing one or more computer software applications. Storage medium 526 can be included in workstations 520 or physically remote from workstations 520. For example, storage medium 526 can be accessible by workstations 520 through a wired or wireless network connection.

Storage medium 526 includes a set of instructions for a computer. The set of instructions includes one or more routines capable of being run or performed by workstations 520. The set of instructions can be embodied in one or more software applications or in computer code.

Data storage 510 can be implemented using a variety of devices for storing electronic information such as a file transfer protocol ("FTP") server, for example. Data storage 510 includes electronic data. For example, data storage 510 can store patient exam images and/or other information, electronic medical records, patient orders, etc., for a plurality of patients. Data storage 510 may include and/or be in communication with one or more clinical information systems, for example.

Communication between workstations 520, workstations 520 and data storage 510, and/or a plurality of data stores 510 can be via any one or more types of known networks including a local area network ("LAN"), a wide area network ("WAN"), an intranet, or a global network (for example, Internet). Any two of workstations 520 and data stores 510 can be coupled to one another through multiple networks (for example, intranet and Internet) so that not all components of system 500 are required to be coupled to one another through the same network.

Any workstations 520 and/or data stores 510 can be connected to a network or one another in a wired or wireless fashion. In an example embodiment, workstations 520 and data store 510 communicate via the Internet and each workstation 520 executes a user interface application to directly connect to data store 510. In another embodiment, workstation 520 can execute a web browser to contact data store 510. Alternatively, workstation 520 can be implemented using a device programmed primarily for accessing data store 510.

Data storage 510 can be implemented using a server operating in response to a computer program stored in a storage medium accessible by the server. Data storage 510 can operate as a network server (often referred to as a web server) to communicate with workstations 520. Data storage 510 can handle sending and receiving information to and from workstations 520 and can perform associated tasks. Data storage 510 can also include a firewall to prevent unauthorized access and enforce any limitations on authorized access. For instance, an administrator can have access to the entire system and have authority to modify portions of system 500 and a staff member can only have access to view a subset of the data stored at data store 510. In an example embodiment, the administrator has the ability to add new users, delete users and edit user privileges. The firewall can be implemented using conventional hardware and/or software.

Data store 510 can also operate as an application server. Data store 510 can execute one or more application programs to provide access to the data repository located on data store 510. Processing can be shared by data store 510 and workstations 520 by providing an application (for example, a java applet). Alternatively, data store 510 can include a stand-alone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 510 can be implemented using a variety of devices for storing electronic information such as an FTP server. It is understood that the storage device can be implemented using memory contained in data store 510 or it may be a separate physical device. The storage device can include a variety of information including a data warehouse containing data such as patient medical data, for example.

Data storage 510 can also operate as a database server and coordinate access to application data including data stored on the storage device. Data storage 510 can be physically stored as a single database with access restricted based on user characteristics or it can be physically stored in a variety of databases.

In an embodiment, data storage 510 is configured to store data that is recorded with or associated with a time and/or date stamp. For example, a data entry can be stored in data storage 510 along with a time and/or date at which the data was entered or recorded initially or at data storage 510. The time/date information can be recorded along with the data as, for example, metadata. Alternatively, the time/date information can be recorded in the data in manner similar to the remainder of the data. In another alternative, the time/date information can be stored in a relational database or table and associated with the data via the database or table.

In an embodiment, data storage 510 is configured to store image and/or other medical data for a patient. The medical data can include data such as numbers and text. The medical data can also include information describing medical events. For example, the medical data/events can include a name of a medical test performed on a patient. The medical data/events can also include the result(s) of a medical test performed on a patient. For example, the actual numerical result of a medical test can be stored as a result of a medical test. In another example, the result of a medical test can include a finding or analysis by a caregiver that entered as text.

Thus, certain embodiments provide adaptive, machine learning systems and methods for hanging/display protocol determination. Certain embodiments provide a technical effect of using high level characteristics and individual image header data to classify an image study and determine an appropriate hanging/display protocol for study image display, for example. Certain embodiments help to provide a more accurate or appropriate "apples to apples" comparison of images on a display for a user.

Certain embodiments use high level characteristics that help provide image comparison rules rather than only relying on individual DICOM data elements so that the analysis is robust to changes in image acquisition techniques. High level characteristics are less like to change much over time and are therefore more robust to introduction of new acquisition techniques. High level characteristics about a study are determined based on information from series in the study and relationships between the series. High level concept models can be more resilient to small deviations in image acquisition techniques and therefore can be more accurate in classifying the study.

Certain embodiments use machine learning techniques to map a high level concept model to an image display layout. Machine learning techniques allow for introduction new high level models or layouts and can intelligently evolve based on the new changes without manual changing of hanging protocol analysis and selection rules.

Prior hanging protocol rules are explicitly configured for modality, body parts, exam procedures, historical count, and monitor count. The many variables that need to be accounted for many involve many permutations of hanging protocols. Using high level characteristics as guidelines for hanging protocols, explicit rules for all of the individual variables listed above may be eliminated.

The explicit rules rely on a deterministic model thus making them inflexible to change. Instead, high level characteristics can also be used to model the study. The high level characteristics are determined based on the series information and the relationship between the series of images. Then, the high level conceptual model of the study is mapped to a layout based on machine learning algorithms leveraging from prior layouts. In certain embodiments, a machine learning based algorithm relies on a probabilistic model that can accommodate inexact matches.

In certain embodiments, hanging/display protocols are automatically created based on the general high level characteristics rules. These hanging/display protocols can continue to adapt to the user's needs as image acquisition changes. For example, certain embodiments can capture a history of how the user has used a workstation and displayed images and adapt a hanging/display protocol to provide the user with images and other data according to that user's preferences.

While certain examples above discuss hanging protocols and/or display protocols, certain examples can apply to both types of display configuration.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

For example, certain embodiments may provide a machine-readable storage medium including a set of instructions for execution on a processor. The set of instructions may include, for example, an input routine receiving one or more images in an image study for display. The set of instructions may also include a machine learning routine selecting a hanging protocol for display of the one or more images. The set of instructions may also include an output routine providing the hanging protocol for use in displaying the one or more images.

In certain embodiments, the machine learning routine captures one or more high level characteristics for the image study based on relationships between images in the study. The machine learning routine identifies one or more low level characteristics for individual images in the image study. The machine learning routine classifies the image study based on a combination of the high level characteristics and the low level characteristics. The machine learning routine determines a hanging protocol for the image study based on the classifying.

In certain embodiments, the one or more high level characteristics include detection method, number of relevant images, and/or a comparison of image resolution versus monitor resolution, for example. In certain embodiments, the one or more low level characteristics include header data elements, such as DICOM header data elements, and/or order information, such as HL-7 order information, for example.

In certain embodiments, the machine learning routine adapts the hanging protocol based on a stored user layout of images. In certain embodiments, the machine learning routine determines a hanging protocol by determining a methodology to detect abnormalities in the image study. The methodology can be determined by displaying images with different views from the image study, displaying relevant images to support the methodology from one or more additional image studies, and limiting a number of images displayed.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for determining a hanging protocol for clinical image display, said method comprising:
   capturing one or more high level characteristics for an image study based on relationships between images in the study;
   identifying one or more low level characteristics for individual images in the image study;
   classifying the image study based on a combination of the high level characteristics and the low level characteristics;
   determining a hanging protocol for the image study based on the classifying; and
   providing the hanging protocol for display of images in the image study.

2. The method of claim 1, wherein the one or more high level characteristics comprise at least one of detection method, number of relevant images, and a comparison of image resolution versus monitor resolution.

3. The method of claim 2, wherein detection method comprises at least one of comparison with historical study, three-dimensional dataset perspective views, three-dimensional extrapolation from a two-dimensional image, pre-contrast and post-contrast injection views, pre-exercise and post-exercise views, and temporal based navigation.

4. The method of claim 1, wherein the one or more low level characteristics comprise at least one of header data elements and order information.

5. The method of claim 1, further comprising adapting the hanging protocol based on a stored user layout of images.

6. The method of claim 1, wherein determining a hanging protocol further comprises determining a hanging protocol for the image study by applying a machine learning algorithm to the combination of the high level characteristics and the low level characteristics.

7. The method of claim 6, wherein the machine learning algorithm utilizes a probabilistic model to apply one or more high level characteristics for the image study based on image study information and relationships between images in the study with one or more low level characteristics for individual images in the image study.

8. The method of claim 6, wherein the machine learning algorithm is implemented using an artificial neural network to store and evolve correlations between the high level characteristics and layout.

9. The method of claim 1, further comprising allowing a user to modify a layout automatically generated based on the hanging protocol.

10. The method of claim 1, wherein the determining a hanging protocol further comprises determining a methodology to detect abnormalities in the image study, the method further comprising:
    displaying images with different views from the image study;
    displaying relevant images to support the methodology from one or more additional image studies; and
    limiting a number of images displayed.

11. A machine-readable storage medium including a set of instructions for execution on a processor, the set of instructions, when executed, to implement a method for determining a hanging protocol for clinical image display, said method comprising:
    capturing one or more high level characteristics for an image study based on relationships between images in the study;
    identifying one or more low level characteristics for individual images in the image study;
    classifying the image study based on a combination of the high level characteristics and the low level characteristics;
    determining a hanging protocol for the image study based on the classifying; and
    providing the hanging protocol for display of images in the image study.

12. The machine readable storage medium of claim 11, wherein the one or more high level characteristics comprise at least one of detection method, number of relevant images, and a comparison of image resolution versus monitor resolution.

13. The machine readable storage medium of claim 12, wherein detection method comprises at least one of comparison with historical study, three-dimensional dataset perspective views, three-dimensional extrapolation from a two-dimensional image, pre-contrast and post-contrast injection views, pre-exercise and post-exercise views, and temporal based navigation.

14. The machine readable storage medium of claim 11, wherein the one or more low level characteristics comprise at least one of header data elements and order information.

15. The machine readable storage medium of claim 11, further comprising adapting the hanging protocol based on a stored user layout of images.

16. The machine readable storage medium of claim 11, wherein determining a hanging protocol further comprises determining a hanging protocol for the image study by applying a machine learning algorithm to the combination of the high level characteristics and the low level characteristics.

17. The machine readable storage medium of claim 16, wherein the machine learning algorithm utilizes a probabilistic model to apply one or more high level characteristics for the image study based on image study information and relationships between images in the study with one or more low level characteristics for individual images in the image study.

18. The machine readable storage medium of claim 16, wherein the machine learning algorithm is implemented using an artificial neural network to store and evolve correlations between the high level characteristics and layout.

19. The machine readable storage medium of claim 11, further comprising allowing a user to modify a layout automatically generated based on the hanging protocol.

20. The machine readable storage medium of claim 11, wherein the determining a hanging protocol further comprises determining a methodology to detect abnormalities in the image study, the method further comprising:
- displaying images with different views from the image study;
- displaying relevant images to support the methodology from one or more additional image studies; and
- limiting a number of images displayed.

\* \* \* \* \*